US00PP20592P2

(12) United States Plant Patent
Utecht

(10) Patent No.: US PP20,592 P2
(45) Date of Patent: Dec. 22, 2009

(54) ***PELARGONIUM* PLANT NAMED 'FISBILDEEP'**

(50) Latin Name: *Pelargonium peltatum (L.) L'Hérit ex Ait*
Varietal Denomination: Fisbildeep

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/228,955

(22) Filed: Aug. 18, 2008

(51) Int. Cl.
*A01H 5/00* (2006.01)

(52) U.S. Cl. ..... Plt./332

(58) Field of Classification Search ..... Plt./332
See application file for complete search history.

(56) References Cited

OTHER PUBLICATIONS

Upov Plant Variety Database 2009/02 page 1a and 1b.*

* cited by examiner

*Primary Examiner*—Annette H Para
(74) *Attorney, Agent, or Firm*—S. Matthew Edwards

(57) ABSTRACT

A new *Pelargonium* plant named 'Fisbildeep,' particularly distinguished by the double-type, medium sized, dark-red flowers, floriferous with relatively small inflorescences, medium green foliage, leaves with rounded lobes and weak zonation, medium to strong vigor, and mounding to semi-trailing, tight and compact plant habit.

1 Drawing Sheet

Latin name of the genus and species of the plant claimed: *Pelargonium peltatum* (*L.*) *L 'Hérit ex Ait.*

Varietal denomination: 'Fisbildeep'.

BACKGROUND OF THE NEW PLANT

The present invention comprises a new ivy *Geranium* plant, botanically known as *Pelargonium peltatum* and hereinafter referred to by the variety name 'Fisbildeep.'

'Fisbildeep' is a product of a planned breeding program. The new cultivar has dark-red, double flowers, medium green foliage with weak zonation, and semi-trailing, relatively tight and compact plant habit.

'Fisbildeep' originated from a hybridization made in the late summer of 2003 in a controlled breeding program in Hillscheid, Germany. The female parent was the commercial variety 'Ruby Dream,' U.S. Plant Pat. No. 17,813, 'Fisruby.' 'Fisruby' has dark-red, double flowers, deep green foliage with distinct zonation, and moderately vigorous growth.

The male parent of 'Fisbildeep' was the commercial variety 'Colorcade Coral Pink,' U.S. Plant Pat. No. 13,563, 'Balcolcork.' 'Balcolcork' has salmon-pink to light carmine-red, double flowers, zoned foliage, and about medium sized mounding and trailing plant habit.

'Fisbildeep' was selected as one flowering plant within the progeny of the stated cross in the spring of 2004 in a controlled environment in Galdar, Gran Canaria, Spain.

The first act of asexual reproduction of 'Fisbildeep' was accomplished when vegetative cuttings were taken from the initial selection in the fall of 2004 in a controlled environment in Galdar, Gran Canaria, Spain.

Horticultural examination of plants grown from cuttings of the plant initiated in March 2005 in Hillscheid, Germany, and continuing thereafter, has demonstrated that the combination of characteristics as herein disclosed for 'Fisbildeep' are firmly fixed and are retained through successive generations of asexual reproduction.

'Fisbildeep' has not been observed under all possible environmental conditions. The phenotype may vary significantly with variations in environment such as temperature, light intensity and day length.

Plant Breeder's Rights for this cultivar was applied for in Canada on Mar. 30, 2007 and in Germany on Feb. 21, 2007. 'Fisbildeep' has not been made publicly available more than one year prior to the filing of this application.

DESCRIPTION OF THE DRAWING

The accompanying photographic drawing shows typical flower and foliage characteristics of 'Fisbildeep' with colors being as true as possible with an illustration of this type. The photographic drawing shows a flowering potted plant of the new variety.

DETAILED BOTANICAL DESCRIPTION

The measurements were taken in Hillscheid, Germany, on May 11, 2007 on plants that were growing in a greenhouse. Culture of these plants started in mid February 2007, when rooted cuttings were planted into 12 cm pots, were pinched once in late February, and grown out at a minimum day/night temperature of (only) 14° C. until mid April, and at higher temperatures thereafter.

Color Chart used: Royal Horticultural Society Colour Chart (R.H.S.) 2001

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* (common name: ivy *Geranium*) as a new and distinct variety.

1. Medium sized, dark-red colored flowers
2. Double-type with many petals, initially rose-bud-like
3. Small, semi-spherically shaped inflorescences, relatively low above the foliage
4. Medium green foliage, leaves with rounded lobes and with weak zone
5. Medium to strong vigor, and mounding to semi-trailing, tight and compact plant habit.
6. Mid season begin of flowering, and floriferous throughout the summer

TABLE 1

DIFFERENCES BETWEEN THE NEW VARIETY 'FISBILDEEP' AND SIMILAR VARIETIES:

| | 'Fisbildeep' | 'Fisruby' (U.S. Plant Pat. No. 17,813) | 'Freestyle Ruby Red' ('Free Rured,' U.S. Plant Pat. No. 18,042) |
|---|---|---|---|
| Flower color | Closest to RHS 46A | RHS 46A | RHS 46A-46B, overall view is closer to 46B |
| Number of petals | 25-30 | 15-18 | 20-30 |
| Umbel diameter | 7.7 cm | 11.9 cm | 8.0 cm |
| Plant habit | Compact, tight, medium sized or over | Less tight, less compact, with longer, trailing branches | Compact, tight, medium sized |

Plant:

*Form, growth and habit.*—Initially semi-upright.
*Plant height.*—15.3 cm.
*Plant height* (*inflorescence included*).—21 cm.
*Plant diameter.*—25 cm.
*Plant size at the end of the summer* (*about 6 months old, plant spread from base of the main stem to the shoot tips*).—55–65 cm.

Stem:

*Number of branches.*—6.8.
*Color of stem.*—Green, RHS 137D, no anthocyanin.
*Length of stem.*—About 15–20 cm.
*Diameter.*—4–5 mm.
*Length of internodes.*—3–5 cm.
*Texture.*—Covered with fine short hair.

Foliage:

*Immature, leaf color, upper surface.*—RHS 143A
*Lower surface.*—RHS 143B.
*Mature, leaf color, upper surface.*—Medium green, RHS 137C to 137D Lower surface: RHS 137D.
*Length.*—4.5 cm.
*Width* 7.5 cm.
*Shape.*—Ivy shaped with distinct, rounded lobes.
*Base shape.*—Cordate.
*Apex shape.*—Rounded lobes.
*Margin.*—Entire.
*Texture.*—Appears smooth, but upper side covered with sparse, fine, short hair, lower side hirtellous (short, upright hair).
*Color of zone.*—Weak.
*Color of veins, upper surface.*—Indistinct, approximately RHS 144A.
*Color of veins, lower surface.*—Light green, RHS.
*Petiole color.*—RHS 137D.
*Petiole length.*—Most often between 3 and 4.5 cm.
*Diameter of petiole.*—2 mm.
*Texture.*—Very short, fine hair.

Inflorescence:

*Begin of flowering* (50% *of plants with open flowers*).—May 2 (12 weeks old).
*Duration of flowering.*—Continuous flowering throughout the Summer.
*Type and shape of inflorescence.*—Umbel, nearly semi-spherical, tight, relatively small.
*Number of inflorescences per plant.*—2–3 at the stated time, approx. 25 in late summer.
*Number of flowers and buds per inflorescence.*—Most often 15–20.
*Umbel diameter.*—7.7 cm.
*Umbel depth.*—5.2 cm.
*Color of peduncle.*—Green, RHS 143A to 143B.
*Length of peduncle.*—12.1 cm.
*Peduncle diameter.*—3 mm.
*Texture.*—Covered with very short hair.
*Color of pedicel.*—Green, RHS 143B, no anthocyanin.
*Length of pedicel.*—1.9 cm.
*Diameter of pedicel.*—1.5 mm.
*Texture.*—Densely covered with short hair.

Corolla:

*Form.*—Double-type, round, with relatively many petals, initially rose-shaped.
*Diameter of flower.*—4.2 cm.
*Depth of flower.*—1.5–2.0 cm.
*Number of petals.*—Approximately 25 to 30.
*Color upper petals, upper surface.*—RHS 46A or intermediate between RHS 46A and 46B, overlain with a blackish shimmer, near RHS 187A, At the base very dark veins, RHS 187A.
*Color upper petals, lower surface.*—Deep red, between RHS 46B and 53B.
*Length of upper petals.*—23–25 mm.
*Width of upper petals.*—15–18 mm.
*Color lower petals, upper surface.*—Between RHS 46A and 46B, and with a blackish shimmer, RHS 187A.
*Color lower petals, lower surface.*—Deep red, between RHS 46B and 53B.
*Length of lower petals.*—23–25 mm.
*Width of lower petals.*—16–19 mm.
*Petal shape.*—Obovate.
*Apex shape.*—Rounded.
*Margin.*—Entire.
*Base.*—Acute.
*Petal texture.*—Smooth.
*Number of petaloids.*—0 to 2, narrower and shorter than petals.
*Color of petaloids.*—Similar as petals, or of somewhat less intense hue.

Bud (just before opening):

*Color.*—Dark red, RHS 46A or 53A.
*Length.*—19–21 mm.
*Width.*—12–16 mm.
*Shape.*—Initially nearly round, elliptical at opening.

Calyx:

*Number of sepals.*—Most often 6 or 7.
*Color of sepals.*—Abaxial green, RHS 143C, adaxial RHS 144C, no anthocyanin.
*Length of sepals.*—9–10 mm.
*Width of sepals.*—5 mm for the largest sepal, 2–3 mm for the other sepals.
*Sepal shape.*—Lanceolate.
*Apex shape.*—Acute to acuminate.

*Margins.*—Entire.

*Texture.*—Covered with relatively long, short hair.

Reproductive organs:

*Pistil.*—One.

*Length.*—10 mm.

*Style color.*—Whitish to pale pink, RHS 69C.

*Style length.*—3–4 mm.

*Stigma color.*—Dark purple, RHS 187B.

*Number of anthers.*—None or up to 3.

*Length of anthers.*—2 mm.

*Anther color.*—Purple, N79C.

*Length filaments.*—8 mm.

*Color of filaments.*—White to pale pink, RHS 68B, at upper end.

*Pollen amount.*—Relatively little per flower.

*Color of pollen.*—Yellow-orange, RHS 25A.

*Fertility/seed set.*—No seed set observed.

Disease/pest resistance: Disease resistance or susceptibility other than typical for the species has not been observed on this hybrid.

What is claimed is:

1. A new and distinct variety of *Pelargonium* plant named 'Fisbildeep,' substantially as illustrated and described herein.

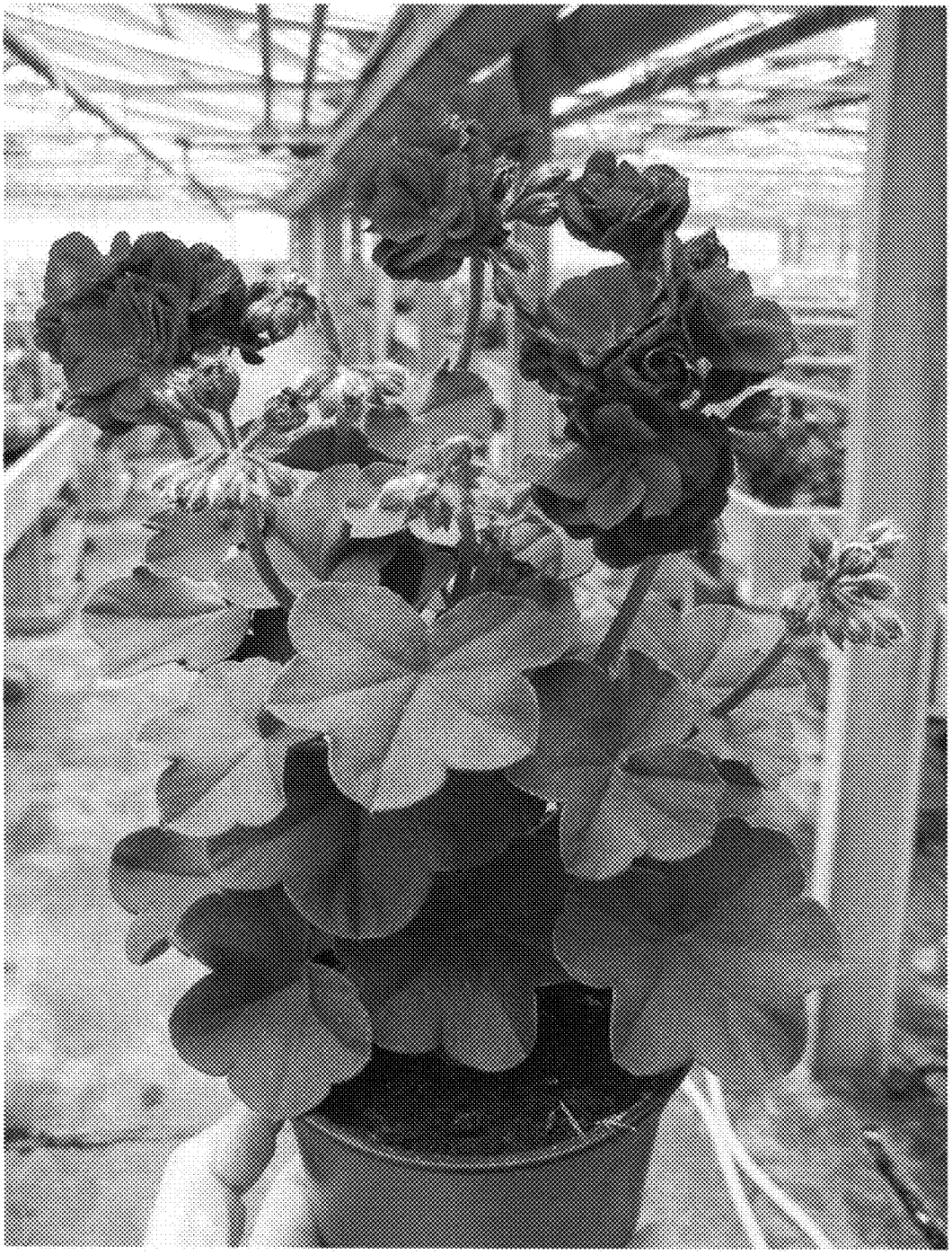

* * * * *